United States Patent [19]

Cooper

[11] Patent Number: 5,250,531

[45] Date of Patent: Oct. 5, 1993

[54] DIHYDROPYRIMIDINE ANTIALLERGY AGENTS

[75] Inventor: Kelvin Cooper, Noank, Conn.

[73] Assignee: Pfizer Inc., New York, N.Y.

[21] Appl. No.: 752,524

[22] PCT Filed: Mar. 9, 1990

[86] PCT No.: PCT/EP90/00392

§ 371 Date: Aug. 29, 1991

§ 102(e) Date: Aug. 29, 1991

[87] PCT Pub. No.: WO90/11281

PCT Pub. Date: Oct. 4, 1990

[30] Foreign Application Priority Data

Mar. 17, 1989 [GB] United Kingdom ........... 8906168

[51] Int. Cl.$^5$ ............... C07D 401/10; C07D 403/10; C07D 413/10; A61K 31/505
[52] U.S. Cl. ................... 514/256; 544/333; 544/316; 544/318; 544/331; 514/274; 514/275
[58] Field of Search ............ 514/274, 272, 256, 275; 544/316, 318, 331, 332, 333

[56] References Cited

FOREIGN PATENT DOCUMENTS 202654 11/1986 European Pat. Off. .
294074 12/1988 European Pat. Off. .

*Primary Examiner*—John M. Ford
*Attorney, Agent, or Firm*—Peter C. Richardson; Gregg C. Benson; James T. Jones

[57] ABSTRACT

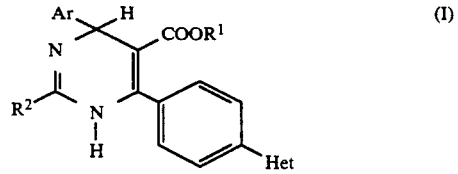

A compound of formula (I), where Ar is optionally substituted phenyl or methylenedioxyphenyl or benzothienyl, $R^1$ is alkyl, $R^2$ is selected from hydroxy, alkoxy, alkylthio, alkyl and optionally substituted phenyl or amino, and "Het" is a heterocyclic group. The compounds are platelet activating factor inhibitors.

9 Claims, No Drawings

DIHYDROPYRIMIDINE ANTIALLERGY AGENTS

This invention relates to certain 1,4-dihydropyrimidines. These compounds are potent and selective antagonists of platelet activating factor having clinical utility in the treatment of allergic and inflammatory conditions in humans and animals.

Platelet activating factor (PAF) 1-0-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutropbils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This, coupled with evidence showing that circulating PAF levels are increased by endotoxin infusion, indicates that PAF is a prime mediator in certain forms of shock. Intravenous infusion of PAF at doses of 20-200 pmol kg$^{-1}$ min$^{-1}$ into rats results in the formation of extensive haemorrbagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. Also increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and, in guinea pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise the actions of PAF, will be of value in the treatment of the above conditions.

According to the present invention there are provided compounds of the formula:

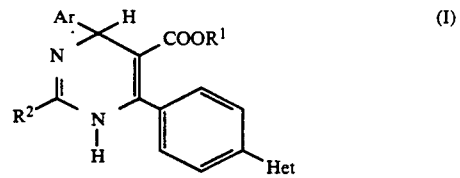

and their pharmaceutically acceptable salts;

where Ar is either (a) phenyl optionally substituted by 1 to 3 substituents each independently selected from nitro, halo, trifluoromethyl, $C_1$-$C_4$ alkyl, $C_1$-$C_4$ alkoxy, fluoro-($C_1$-$C_4$ alkoxy), $C_1$-$C_4$ alkylthio, $C_1$-$C_4$ alkylsulphonyl, hydroxy and cyano, or (b) methylenedioxyphenyl or benzothienyl;

$R^1$ is $C_1$-$C_4$ alkyl;

$R^2$ is hydroxy; $C_1$-$C_4$ alkoxy; $C_1$-$C_4$ alkylthio; $C_1$-$C_4$ alkyl; phenyl optionally substituted by 1 or 2 halo substituents; or a group of the formula —$NR^3R^4$ where $R^3$ and $R^4$ are each independently H or $C_1$-$C_4$ alkyl;

and "Het" is a 5- or 6-membered aromatic heterocyclic group containing one or more nitrogen atoms and optionally an oxygen or sulphur atom in its ring and which is optionally fused to a benzene ring or to a further 5- or 6-membered aromatic heterocyclic ring containing one or more nitrogen atoms or an oxygen or sulphur atom in its ring, either or both of said rings being optionally substituted with up to three substituents each independently selected from $C_1$-$C_4$ alkyl, $C_1$-$C_4$ alkoxy, halo, trifluoromethyl and cyano.

In the definitions given herein, the term halo means fluoro, chloro, bromo or iodo. Alkyl and alkoxy groups of 3 or more carbon atoms may be straight or branched-chain.

"Het" is preferably an imidazolyl, thiazolyl, oxazolyl, triazolyl, pyridyl, benzimidazolyl, imidazopyridyl or imidazotbiazolyl group, all these groups being optionally substituted as defined for formula (I).

Typical examples of "Het" are 2-methylimidazor4,5-c]pyrid-1-yl, 2-trifluoromethylimidazo-[4,5-c]pyrid-l-yl, 2-n-buthylimidazo [4,5-c]pyrid-1-yl, 3,5-dimethyl-1,2,4-triazol-4-yl, -methylimidazo[4,5-b]pyrid-1-yl, 2-methylimidazo[,2-a]pyrid-3-yl, 2-metbylbenzimidazol-1-yl, 2,4,5-trimethylimidazol-1-yl, 2,4-dimethylthiazol-5-yl, 2,4-dimethyloxazol-5-yl, 2,6-dimethylpyrid-3-yl, and 2-methylimidazo[,2-b]thiazol-3-yl.

When $R^2$ is —OH then the following tautomerism is possible and both tautomers are within the scope of the invention:

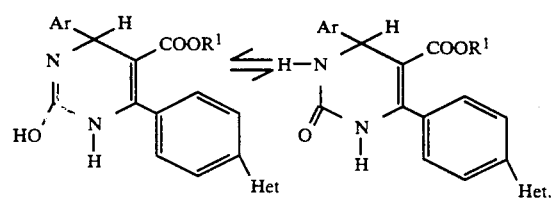

Equally, when $R^3$ and $R^4$ is H, then the following tautomerism is possible and again both tautomers are included:

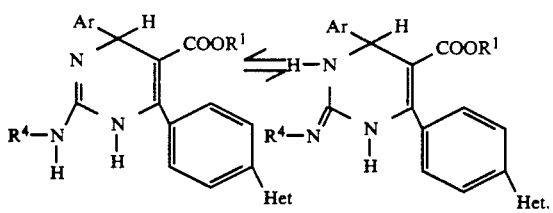

Ar is preferably selected from (i) phenyl substituted by 1 or 2 halo substituents, (ii) methylenedioxyphenyl and (iii) benzothienyl. Ar is most preferably 2-chlorophenyl.

$R^1$ is preferably methyl or ethyl.

$R^2$ is preferably hydroxy, methoxy, methylthio, amino, methylamino, dimethylamino, methyl or phenyl.

"Het" is preferably 2-methylimidazo[4,5-c]pyrid-1-yl.

The compounds of the formula (I) contain at least one asymmetric centre and exist as one or more pairs of enantiomers. Such pairs or individual isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compounds of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

The compounds of formula I may be obtained according to the following reaction scheme:

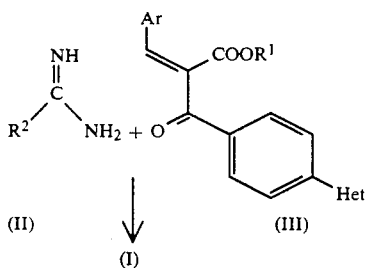

wherein Ar, $R^1$, $R^2$ and Het are as previously defined except that $R^2$ cannot be —OH.

In a typical procedure, the ketoester (III) and the compound (II) are heated together, e.g. at 60°–80° C., in a suitable organic solvent, e.g. ethanol or dimethylformamide, for several hours, optionally in the presence of a base, e.g. sodium bicarbonate. The product of formula (I) can then be isolated and purified by conventional procedures, for example by partition, recrystallisation or by chromatography.

Certain compounds of the formula (I) are conveniently obtained by means of simple chemical transformation reactions. Compounds of formula (I) wherein $R^2$ is $C_1$–$C_4$ alkoxy, preferably methoxy, may be subjected to a conventional dealkylation reaction to yield the corresponding compounds wherein $R^2$ is —OH, e.g. using hydrochloric acid at about room temperature in a suitable organic solvent.

The ketoesters of the formula (III) are either known compounds or can be prepared by methods analogous to those of the prior art, such as the methods described in the preparations given hereafter.

The activity of the compounds of the formula (I) is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6mM $Na_2HPO_4$, 100 Mm NaCl, 0.1% glucose and 0.1% bovine serum albumin, pH 7.25) and finally resuspended in buffer solution to a concentration of $2 \times 10^8$ platelets/ml. A sample (0.5 ml) is preincubated with stirring for two minutes at 37° C. in a Paton aggregometer, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the PAF challenge repeated. The ability of the compound to reduce the bronchoconstrictor effect of PAF is calculated as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2-1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, and a pharmaceutically acceptable diluent or carrier.

The invention also includes a compound of the formula (I), or a pharmaceutically acceptable salt thereof, for use in medicine, in particular for use in the treatment of allergic, inflammatory and hypersecretory conditions in a human being.

The preparation of the compounds of the formula (I) is further illustrated by the following Examples:

EXAMPLE 1

4-(2-Chlorophenyl)1,4-dihydro-5-ethoxycarbonyl-2-methoxy-6-[4-(2-methylimidazo[4,5-c]pyrid-1-yl)phenyl]pyrimidine

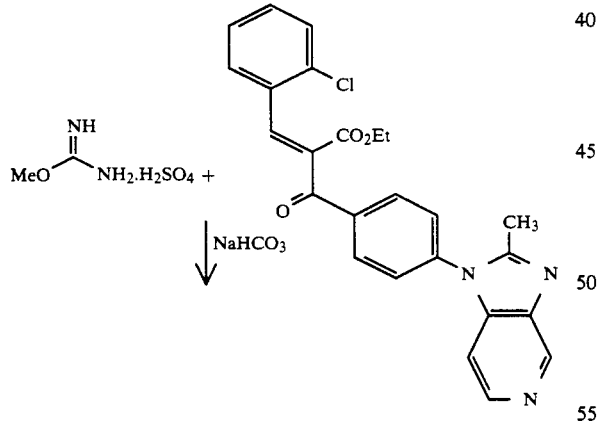

-continued

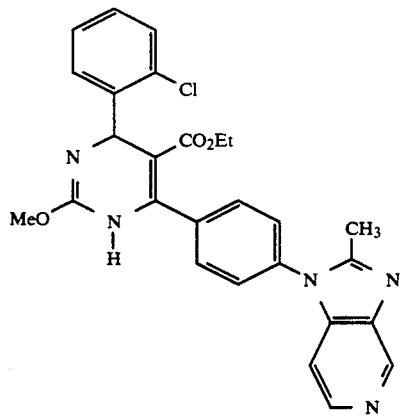

A mixture of 3-(2-chlorophenyl)-2-ethoxycarbonyl-1-[4-(2-methylimidazo[4,5-c]pyrid-1-yl)phenyl]prop-2-ene-1-one (200 mg —see Preparation 1), O-methylisourea hydrogen sulphate (155 mg) and sodium bicarbonate (240 mg) was heated in dimethylformamide (DMF) (5 ml) at 70° C. for 16 hours. The cooled mixture was poured into water (25 ml) and extracted with ethyl acetate (3×25 ml). The combined organic phases were washed with water, dried (MGSO₄), filtered and evaporated and the residue was chromatographed on silica eluting with methylene ebloride/metbanol. The fractions containing the product were combined and evaporated to give the title compound (105 mg), m.p. 228°-232° C.

Analysis %: Found: C,63.48; H, 4.87; N,13.95; Required for $C_{27}H_{24}ClN_5O_3 \cdot \frac{1}{2}H_2O$: C,63.47; H,4.93; N,13.71.

EXAMPLES 2–6

The following compounds were made by the method of Example 1 using the appropriate 3-(aryl-substituted)-propenone and )-methylisourea or S-methlthiourea or substitued guanidine.

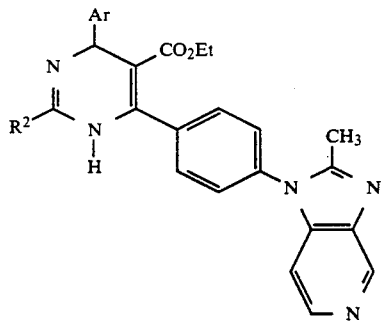

| Example No. | Ar | $R^2$ | m.p. °C. | Analysis % (Theoretical in brackets) | | |
|---|---|---|---|---|---|---|
| | | | | C | H | N |
| 2 | benzodioxole | MeO— | 214–219 | 62.88 (62.97 | 4.91 5.19 | 13.45 # 13.11) |

-continued

| Example No. | Ar | R² | m.p. °C. | Analysis % (Theoretical in brackets) C | H | N |
|---|---|---|---|---|---|---|
| 3 | 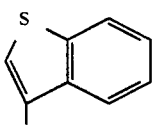 | MeO— | 163-169 | 66.37 (66.52 | 4.82 4.81 | 13.27 13.38) |
| 4 | 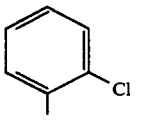 | MeS— | 219-220 | 62.23 (62.6 | 4.57 4.67 | 13.33 13.52) |
| 5 | 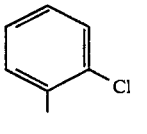 | NH₂— | 215-230 | 61.99 (61.84 | 4.57 4.56 | 16.83 * 16.65) |
| 6 | 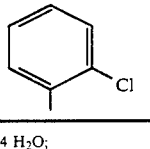 | MeNH— | 150-160 (decomp.) | 62.38 (62.49 | 4.91 4.82 | 16.0 * 16.2) |

\# Analysis for 5/4 H₂O;
\* Analysis for H₂O.

EXAMPLES 7 and 8

The following compounds were made by the method of Example 1 using 3-(2-chlorophenyl)-2-ethoxycarbonyl-1-[4-(2-methylimidazo [4,5-c]pyrid-1-yl)phenyl]-prop-2-ene-1-one and the appropriate amidine hydrochloride.

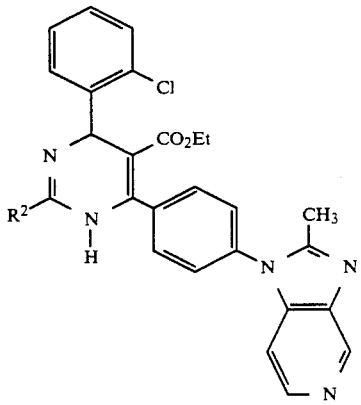

-continued

| Example No. | R² | m.p. (°C.) | Analysis % (Theoretical in brackets) C | H | N |
|---|---|---|---|---|---|
| 7 | Ph— | 274-276 | 69.01 (69 | 4.96 4.89 | 12.34 12.57) |
| 8 | Me— | 175-181 | 66.84 (66.73 | 4.76 4.98 | 14.2 # 14.41) |

\# analysis for 1½ H₂O.

EXAMPLE 9

4-(2-Chlorophenyl)-1,4-dihydro-5-ethoxycarbonyl-6-[4-(2-methylimidazo[4,5-c]pyrid-1-yl)phenyl]pyrimid-2-one

Preparation 1

3-(2-Chlorophenyl)-2-ethoxycarbonyl-1-[4-(2-methylimidazo-[4,5-c]pyrid-1-yl)phenyl]prop-2-ene-1-one

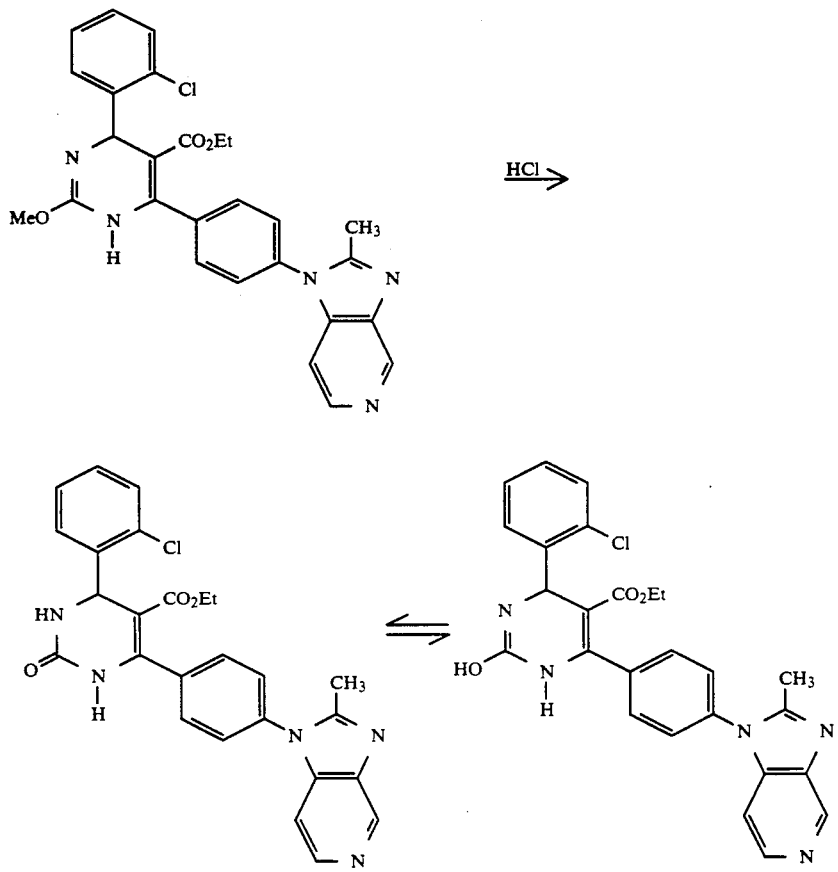

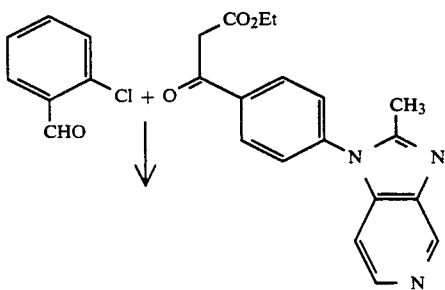

4-(2-Chlorophenyl)-1,4-dihydro-5-ethoxycarbonyl-2-methoxy-6-[4-(2-methylimidazo[4,5-c]pyrid-1-yl)phenyl]pyridine (100 mg) was dissolved in methanol/tetrahydrofuran 1:1 (4 ml) and to the solution 3M hydrochloric acid (2 ml) was added. The solution was stirred at room temperature for 2 hours and the solvent removed in vacuo. The residue was partitioned between ethyl acetate (25 ml) and saturated sodium bicarbonate solution (10 ml) and then the organic phase was dried (MgSO4), filtered and evaporated. The residue was chromatographed on silica eluting with ethyl acetate/diethylamine and the residues containing the product were combined and evaporated to give the title compound (75 mg), m.p. >300° C.

Analysis %: Found: C,60.43; H,4.64; N,13.21; Required for $C_{26}H_{22}ClN_5O_3 \cdot 1\frac{1}{2}H_2O$: C,60.64; H,4.89; N,13.6.

The following Preparations illustrate the preparation of the novel starting materials used in the previous Examples:

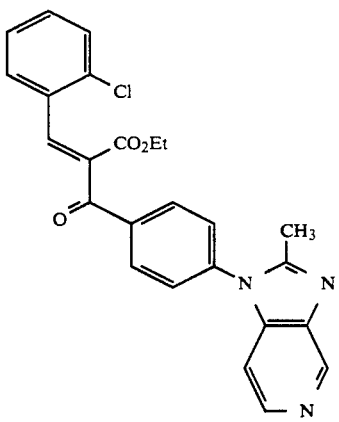

A mixture of 2-chlorobenzaldehyde (2.8 g), ethyl 4'-(2-methylimidazo [4,5-c]pyrid-1-yl)benzoyl acetate (6.4 g—see Preparation 2) and piperidine (100 pl) was stirred at room temperature for 48 hours in acetonitrile (30 ml). The mixture was evaporated to dryness and the residue was chromatographed on silica eluting with ethyl acetate/reethanol (5:1). The fractions containing the product were combined and evaporated to give the title compound, (5.3 g).

N.m.r. (CDCl$_3$, 300 MBz), $\delta$=1.35, (3H, t, J 8 Hz, CH$_3$CH$_2$); 2.53

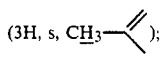

(3H, s, C<u>H</u>$_3$—);

4.27 (2H, d, J 8 Hz, CH$_3$C<u>H</u>$_2$); 7–9.1 (12 H, m).

Preparations 2 and 3

The following compounds were made by the method of Preparation 1 using the appropriate aromatic aldehyde.

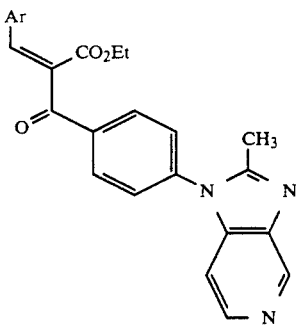

| Preparation No. | Ar | N.m.r. (CDCl$_3$, 300 MHz, =) |
|---|---|---|
| 2 | <img benzodioxole> | 1.38(3H, t, J8Hz); 2.6(3H, s); 4.32(2H, q, J8Hz); 6.02(2H, s); 6.7–9.1(11H, m). |
| 3 | <img thiophene-phenyl> | 1.31(3H, t, J8Hz); 2.58(3H, s); 4.28(2H, q, J8Hz); 7.1–9.1 (13H, m). |

Preparation 4

Ethyl 4'-(2-methylimidazo[4,5-c]pyrid-1-yl)benzoyl acetate

Method A

Essentially the method of Y. Kishi, S. M. Hannick, *J. Org. Chem.*, 1983, 48, 3833.

Zinc dust (894 mg, 13.7 mmol) was suspended in dry tetrahydrofuran (3 ml) under nitrogen and sonicated at room temperature for 10 minutes. Ethyl bromoacetate (2 drops) was added and the mixture was refluxed for 5 minutes. A solution of 1-(4-cyanophenyl)-2-methylimidazo[4,5-c]pyridine (640 mg, 2.74 mmol) in dry tetrahydrofuran (6 ml) was added and the mixture was refluxed for 5 minutes. A solution of ethyl bromoacetate (1.822 g, 10.94 mmol) in dry tetrahydrofuran (2 ml) was added dropwise over 1 hour at reflux, and after a further 10 minutes, the mixture was allowed to cool to room temperature. 50% aqueous potassium carbonate (1 ml) was added and the mixture was stirred for 45 minutes at room temperature, and then filtered through Arbocel filter aid, washing with THF. The filtrate was concentrated under reduced pressure to give a yellow gum. This material was treated with a mixture of 20% aqueous trifluoro acetic acid (10 ml) and dichloromethane (50 ml) at room temperature for 15 minutes. The mixture was neutralised by the addition of saturated aqueous sodium hydrogen carbonate, and then extracted with dichloromethane (2×30 ml). The combined extracts were dried (MGSO$_4$), concentrated under reduced pressure, and the crude product was purified by flash chromatography (eluting with 10–20% methanol in ethyl acetate) to give ethyl 4'-(2-methylimidazor4,5-c]pyrid-1-yl)benzoylacetate (480 mg, 54%) as a yellow gum.

Material obtained by Method A was a white solid, m.p. 111°–112° C. after recrystallisation from ethyl acetate. $^1$H-MMR (300 MHz, CDCl$_3$) 1.32 (3 H, t, J 6 Hz), 2.61 (3 H, s), 4.09 (2 H, s), 4.28 (2 H, q, J 6 Hz), 7.16 (1 H, d, J 6 Hz) 7.55 (2 H, d, J 9 Hz), 8.23 (2 H, d, J 9 Hz), 8.46 (1 H, d, J 6 Hz), 9.09 (1 H, s).

Method B (a) 4-(4-Acetylphenyl)amino-3-nitropyridine hydrochloride

A solution of 4-chloro-3-nitropyridine hydrochloride (9.75 g, 50 mmol) in ethanol (40 ml) was added to a slurry of p-aminoacetophenone (6.76 g, 50 ml) in ethanol (25 ml), and the mixture was stirred at room temperature overnight. The mixture was chilled in ice, and the yellow solid filtered off and dried in vacuo. Yield 10.1 g (69%), m.p. 197°–200° C.

$^1$H-NMR (300 MHz, DMSO-d$_6$) 2.61 (3H, s), 7.19 (1 H, d, J 7 Hz), 7.53 (2 H, d, J 8 Hz), 8.07 (2 H, d, J 8 Hz), 8.33 (1 H, d, J 7 Hz), 9.36 (1 H, s), 10.74 (1 H, s).

(b) 4-(4-Acetylphenyl)amino-3-aminopyridine 4-(4-Acetylphenyl)amino-3-nitropyridine hydrochloride (2.0 g, 71.8 mmol) was partitioned between aqueous sodium hydroxide and dichloromethane (3×20 ml). The combined organic phases were washed with water (20 ml) and concentrated under reduced pressure to give a solid. Ethanol (20 ml) was added, and the solution was hydrogenated over 5% palladium on carbon (0.2 g) at 50 p.s.i. (345 kPa) for 3.5 hours. The catalyst was filtered off, and the solvent removed under reduced pressure to give a brown solid, (1.8 g) which was used directly for the next reaction without purification, m.p. 165°–166° C. (after recrystallisation from ethanol).

$^1$H-NMR (300 MHz, DMSO-$d_6$) 2.47 (3 H, s), 5.00 (2 H, br.s), 7.04 (3 H, m), 7.70 (1 H, br.s), 7.83 (2 H, d, J 8 Hz), 7.98 (1 H, br.s), 8.12 (1 H, s).

(c) 1-(4-Acetyl)phenyl-2-methylimidazo[4,5-c]pyridine

A solution of 4-(4-acetylphenyl)amino-3-aminopyridine (68.0 g, 0.3 mmol) in acetic acid (204 ml) and acetic anhydride (204 ml) was heated at 95° C. for 1.5 hours then cooled and concentrated under reduced pressure. The residue was dissolved in water (500 ml) and rendered basic by the addition of saturated aqueous ammonia. The product was filtered off, washed with water (2×100 ml) and dried in vacuo to give the title compound, (61.0 g, 81%) as a brown solid, m.p. 155°–156° C. (after recrystallisation from water).

$^1$H-NMR (300 MHz, CDCl$_3$), 2.59 (3 H, s), 2.72 (3 H, s), 7.12 (1 H, d, J 5 Hz), 7.53 (2 H, d, J 8 Hz), 8.22 (2 H, d, J 8 Hz), 8.40 (1 H, d, J 5 Hz), 9.04 (1 H, s).

(d) Ethyl 4'-(2-methylimidazo[4,5-c]pyrid-1-yl]benzoylacetate

A solution of 1-(4-acetyl)phenyl-2-methylimidazo[4,5-c]-pyridine (17.5 g, 69.7 mmol) in dry tetrahydrofuran (175 ml) was added to a slurry of sodium hydride (3.68 g, 153 mmol) in a mixture of dry tetrahydrofuran (35 ml) and dimethyl carbonate (24.7 g, 209 mmol) at reflux with stirring over 45 minutes. After a further 1 hour, the mixture was cooled, hexane (200 ml) was added and the resulting precipitate was filtered off and washed with hexane (2×100 ml). The solid was suspended in ethyl acetate (200 ml) and acetic acid (10.2 g) was added. After being stirred for 15 minutes, water (200 ml) was added, and the organic layer was separated. The aqueous phase was extracted with ethyl acetate (100 ml) and the combined organic solutions were washed with water (200 ml), dried (MGSO$_4$) and concentrated to give a gum (17.3 g, 77%). This material could be further purified if desired by flash chromatography (eluting with ethyl acetate:methanol=7:1) to give the title compound as a white solid.

Method C

(a) 4-(2-Methylimidazo[4,5-c]pyrid-1-yl)benzoic acid

A mixture of 1-(4-cyanophenyl)-2-methylimidazo[4,5-c]pyridine (12.0 g, 51.3 mmol) and 40% aqueous sodium hydroxide (55 ml) in absolute ethanol (55 ml) was heated at reflux for 1½ hours. The solvent was removed under reduced pressure, and the brown residue was dissolved in water. The solution was chilled to 0° C. by the addition of ice. Glacial acetic acid (ca 33 ml) was added slowly. The buff solid which precipitated was filtered off, washed with water, and dried in vacuo at 70° C. Yield 9.14 g (70%).

$^1$H-NMR (300 MHz, DMSO-$d_6$) 2.49 (3 H, s), 7.25 (1 H, d, J 6 Hz), 7.72 (2 H, d, J 6 Hz), 8.17 (2 H, d, J 6 Hz), 8.30 (1 H, d, J 6 Hz), 8.92 (1 H, s).

(b) Ethyl 4'-(2-methylimidazo[4,5-c]pyrid-1-yl)-benzoyl acetate

Oxalyl chloride (17.0 ml, 184 mmol) was added to a mixture of 4-(2-methylimidazo[4,5-c]pyrid-1-yl) benzoic acid (11.64 g, 46 mmol) and dry dimethylformamide (0.2 ml) in dry dichloromethane (200 ml) under nitrogen with ice cooling. At the end of the addition, the mixture was sonicated for 1 hour at room temperature, and then concentrated under reduced pressure and re-suspended in dry dichloroethane (200 ml).

In a separate flask, isopropylmagnesium chloride (137 ml of a 2M solution in tetrahydrofuran, 274 mmol) was added dropwise over 20 minutes to a solution of ethyl malonic acid (18.14 g, 137 mmol) in dry dichloromethane (100 ml) at 0° C. After a further 20 minutes, the solution was added at room temperature to the suspension of the acid chloride generated above. The red mixture was sonicated at room temperature for 30 minutes and then cooled in ice whilst 4N hydrochloric acid (250 ml) was added. The mixture was stirred for 10 minutes at room temperature, diluted with dichloromethane (200 ml), and the layers were separated. The aqueous layer was neutralised with saturated aqueous sodium bicarbonate and extracted with dichloromethane (3×200 ml). The combined extracts were dried (MgSO$_4$) and concentrated under reduced pressure to give a yellow gum, which crystallised slowly on standing. Yield 12.10 g (80%).

Preparation 5

1-(4-Cyanophenyl)-2-methylimidazo[4,5-c]pyridine

(a) N-(4-Cyanophenyl)-4-amino-3-nitropyridine

According to the method of *J. C. S. Perkin Trans. I*, 1979, 135, p-cyanoaniline (6.894 g, 58.4 mmol) was added to a solution of 4-chloro-3-nitropyridine (9.26 g, 58.4 mmol) in ethanol (200 ml) and the mixture was stirred at room temperature for 18 hours. The resulting yellow suspension was poured into 500 ml of ice-cold dilute ammonia and filtered. The solid was treated with 150 ml of boiling ethanol, cooled in ice, and filtered to give N-(4-cyanophenyl)-4-amino-3-nitropyridine, 12.15 g, as a bright yellow powder, m.p. 210°–211° C.

$^1$H NMR (CDCl$_3$, 300 MHz): 7.15 (1 H, d, J 6 Hz), 7.45 (2 H, d, J 9 Hz), 7.79 (2 H, d, J 9 Hz), 8.43 (1 H, d, J 6 Hz), 9.36 (1 H, s), 9.80 (1 H, br, s).

(b) 3-Amino-4-(4'-cyanophenyl)aminopyridine

According to a modification of the method of *Pharm. Helv. Acta*, 1975, 50, 188., tin dichloride dihydrate (56.4 g, 250 mmol) was added to a suspension of N-(4-cyanophenyl)-4-amino-3-nitropyridine (12.0 g, 50 mmol) in 2N aqueous hydrochloric acid (35 ml), water (150 ml) and ethanol (75 ml) and the resulting mixture was heated to reflux for 10 minutes under nitrogen. The mixture was cooled in ice, poured into ice-cold 2N aqueous sodium hydroxide (400 ml) and filtered. The creamy-coloured solid was washed with 2N aqueous sodium hydroxide and water, and then dried in a vacuum desiccator. The product, 3-amino-4-(4'-cyanophenyl)aminopyridine, 9.31 g, gradually turns reddish brown on exposure to light and air.

$^1$H NMR (CDCl$_3$, 300 MHz) 3.52 (2 H, br s), 6.04 (1H, br s), 7.03 (2 H, d, J 9 Hz), 7.59 (2 H, d, J 9 Hz), 8.07 (1 H, m), 8.20 (1 H, s).

(c) 1-(4-Cyanophenyl)-2-methylimidazo[4,5-c]pyridine

A mixture of 3-amino-4-(4'-cyanophenyl)aminopyridine (9.31 g, 4.3 mmol), triethyl-orthoacetate (40 ml) and acetic anhydride (30 ml) was heated at reflux for 2 hours under nitrogen, cooled, then concentrated under reduced pressure. The brown residue was dissolved in 1 M hydrochloric acid and washed with ethyl acetate (200 ml). The aqueous layer was rendered basic with saturated aqueous ammonia and extracted with dichloromethane (3×200 ml). The combined extracts were washed with water, dried (MgSO$_4$) and concentrated to give 1-(4-cyanophenyl)-2-methylimidazo[4,5-c] pyridine, 6.5 g, as a brown solid.

$^1$H NMR (CDCl$_3$, 300 MHz): 2.61 (3 H, s), 7.13 (1 H, d, J 6 Hz), 7.58 (2 H, d, J 9 Hz), 7.98 (2 H, d, J 9 Hz), 8.45 (1 H, d, J 6 Hz), 9.11 (1 H, s).

It will be appreciated from the foregoing that what we will claim may include the following:

(1) The compounds of the formula (I) and their pharmaceutically acceptable salts;

(2) Processes as described herein for preparing the compounds of the formula (I) and their salts;

(3) Pharmaceutical compositions comprising a compound of the formula (I), or a pharmaceutically acceptable salt thereof, and a pharmaceutically acceptable diluent or carrier;

(4) A compound of the formula (I), or a pharmaceutically acceptable salt thereof, for use in medicine, particularly for use in the treatment of allergic and inflammatory conditions; and (5) The use of a compound of the formula (I), or of a pharmaceutically acceptable salt thereof, for the manufacture of a medicament for the treatment of allergic and inflammatory conditions.

I claim:

1. A compound of formula (I):

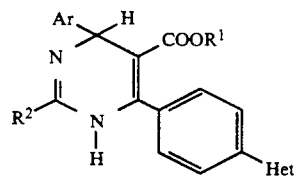

or a pharmaceutically acceptable salt thereof, where Ar is either (a) phenyl optionally substituted by 1 to 3 substituents each independently selected from nitro, halo, trifluoromethyl, C$_1$-C$_4$ alkyl, C$_1$-C$_4$ alkoxy, fluoro-(C$_1$-C$_4$ alkoxy), C$_1$-C$_4$ alkylthio, C$_1$-C$_4$ alkylsulphonyl, hydroxy and cyano, or (b) methylene-dioxyphenyl or benzothienyl; R$^1$ is C$_1$-C$_4$ alkyl; R$^2$ is hydroxy; C$_1$-C$_4$ alkoxy; C$_1$-C$_4$ alkylthio, C$_1$-C$_4$ alkyl; phenyl optionally substituted by 1 or 2 halo substituents; or a group of the formula —NR$^3$R$^4$ where R$^3$ and R$^4$ are each independently H or C$_1$-C$_4$ alkyl; and "Het" is a imidazolyl, thiazolyl, oxazolyl, triazolyl, pyridyl;, benzimidazolyl, imidazopyridyl or imidazothiazolyl group, either or both of the rings thereof being optionally substituted with up to three substituents each independently selected from C$_1$-C$_4$ alkyl, C$_1$-C$_4$ alkoxy, halo, trifluoromethyl and cyano.

2. A compound according to claim 1, wherein Ar is selected from (I) phenyl substituted by 1 or 2 halo substituents, (II) methylenedioxyphenyl and (III) benzothienyl.

3. A compound according to claim 2, wherein Ar is 2-chlorophenyl.

4. A compound according to claim 1, in which R$^1$ is methyl or ethyl.

5. A compound according to claim 1 in which R$^2$ is hydroxy, methoxy, methylthio, amino, methylamino, dimethylamino, methyl or phenyl.

6. A compound according to claim 1, in which "Het" is a 2-methylimidazo[4,5-c]pyrid-l-yl, 2-trifluoromethylimidazo-[4,5-c]pyrid -1-yl, 2-n-butyl-imidazo[4,5-c]pyrid-1-yl, 3,5-dimethyl1,2,4-triazol-4-yl, '1-methylimidazo[4,5-]pyrid-1-yl, 2-methylimidazo[1,2-a]pyrid-3-yl, 2-methyl benzimidazol-1-yl, 2,4,5-trimetiiylimidazol-1-yl, 2,4-dimethyl thiazol-5-yl, 2,4-dimetliyloxazol-5-yl, 2,6-dimethylpyrid-3-yl or 2-methylimidazo[1,2-blthiazol-3-yl group.

7. A compound according to claim 6, in which "Het" is 2-methylimidazo[4,5-c]pyrid-1-yl.

8. A method of treating allergic or inflammatory conditions, which comprises administering to a patient an effective amount of a compound according to claim 1.

9. A pharmaceutical composition comprising a compound according to claim 1, or a pharmaceutically acceptable salt thereof, and a pharmaceutically acceptable diluent or carrier.

* * * * *